US008479559B2

(12) United States Patent
Miklos et al.

(10) Patent No.: US 8,479,559 B2
(45) Date of Patent: Jul. 9, 2013

(54) CYLINDRICAL PHOTOACOUSTIC DETECTOR WITH EXCITATION OF THE SECOND AZIMUTHAL RESONANCE

(75) Inventors: Andras Miklos, Stuttgart (DE); Judit Angster, Stuttgart (DE)

(73) Assignee: Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 559 days.

(21) Appl. No.: 12/593,145

(22) PCT Filed: Mar. 27, 2008

(86) PCT No.: PCT/EP2008/002439
§ 371 (c)(1),
(2), (4) Date: Sep. 25, 2009

(87) PCT Pub. No.: WO2008/116659
PCT Pub. Date: Oct. 2, 2008

(65) Prior Publication Data
US 2010/0107732 A1    May 6, 2010

(30) Foreign Application Priority Data
Mar. 27, 2007   (DE) .................. 10 2007 014 517

(51) Int. Cl.
*G01N 21/17* (2006.01)
*G01N 23/06* (2006.01)
*G01J 5/58* (2006.01)

(52) U.S. Cl.
USPC ..... 73/24.02; 73/24.06; 356/336; 250/339.07

(58) Field of Classification Search
USPC .............. 73/643, 579, 24.02, 24.06; 356/438, 356/440, 336; 250/339.07
See application file for complete search history.

(56) References Cited

U.S. PATENT DOCUMENTS

| 3,938,365 A * | 2/1976 | Dewey, Jr. ............... 73/24.02 |
| 4,818,882 A * | 4/1989 | Nexo et al. ................ 250/343 |
| 2006/0123884 A1* | 6/2006 | Selker et al. ............. 73/24.02 |
| 2010/0103425 A1 | 4/2010 | Miklos et al. |
| 2010/0107733 A1 | 5/2010 | Miklos et al. |

FOREIGN PATENT DOCUMENTS

| EP | 1715324 | 10/2006 |
| WO | 97/15817 | 5/1997 |
| WO | 2004/008113 | 1/2004 |

OTHER PUBLICATIONS

Goldan P D et al. "An Acoustically Resonant System for Detection of Low-Level Infrared Absorption in Atmospheric Pollutants" Journal of Applied Physics, American Institute of Physics. New York, US, vol. 45, No. 10 Oct. 1, 1974 p. 4350-4355, XP001167333 ISSN: 0021-8979 Figure 5; Table I p. 4352, right-hand column.

A. Petzold et al. "Photoacoustic soot sensor for in-situ black carbon monitoring" Applied Physics B, vol. 63, 1996, pp. 191-197, XP002485551 abstract; figure 1.

(Continued)

*Primary Examiner* — Peter Macchiarolo
*Assistant Examiner* — Rose M Miller
(74) *Attorney, Agent, or Firm* — Greenblum & Bernstein, P.L.C.

(57) ABSTRACT

A photoacoustic detection device includes a cylindrical acoustic resonator having an arrangement for guiding light essentially perpendicular to a cylinder axis in such a manner that a second azimuthal resonance of cylinder oscillation is excitable by absorption of the light.

24 Claims, 5 Drawing Sheets

OTHER PUBLICATIONS

Petzold A et al. "Novel Design of a Resonant Photoacoustic Spectrophone for Elementalcarbon Mass Monitoring" Applied Physics Letters, AIP, American Institute of Physics, Melville, NY, vol. 66, No. 10, Mar. 6, 1995, pp. 1285-1287, XP000503665 ISSN: 0003-6951 figure 2.

Miklos A et al. "Windows Resonant Acoustic Chamber for Laser-Photoacoustic Applications" Applied Physics B. Photophysics and Chemistry, Springer Verlag. Heidelberg, DE, vol. B48, No. 3, Mar. 1, 1989, pp. 213-218 XP000035737 figure 1.

Miklos A et al. "Application of a wavelength-amplitude double-modulation method in photoacoustic detection using a pulsed optical parametric oscillator" pp. 579-581.

Miklos A et al. "Multipass acoustically open photoacoustic detector for trace gas measurements" pp. 2529-2534, Apr. 2006.

* cited by examiner

CYLINDRICAL PHOTOACOUSTIC DETECTOR WITH EXCITATION OF THE SECOND AZIMUTHAL RESONANCE

CROSS-REFERENCE TO RELATED APPLICATIONS

The present application is a U.S. National Stage of International Patent Application No. PCT/EP2008/002439 filed Mar. 27, 2008 which published as WO 2008/116659 on Oct. 2, 2008, and claims priority of German Patent Application No. 10 2007 014 517.0 filed Mar. 27, 2007.

BACKGROUND OF THE INVENTION

1. Field of the Invention

The invention relates to a photoacoustic detector that is constructed as a cylinder and in which the second azimuthal resonance oscillation is used to enhance the acoustic signal.

2. Discussion of Background Information

Photoacoustic measuring methods, i.e., measuring methods in which the gas that is to be investigated is irradiated with a light source and heated by absorption, are highly suitable for precise measurements of the concentration of absorbent substances, especially absorbent substances in gases. The gas expands when it is heated. If heating, and hence expansion, are periodic, a sound wave is formed and this sound wave can be measured by a sound pressure sensor.

Photoacoustic spectroscopy has several advantages over classic absorption spectroscopy in which the light passing through the sample is measured, and the absorption is inferred from the difference between the incoming light and the light passing through the sample. The photoacoustic signal is linear within a concentration range of approximately 5-6 orders of magnitude. The sensitivity of the detector is independent of the wavelength of the excitation light. A photoacoustic detector with comparable sensitivity is smaller and cheaper than a classic optical absorption spectroscopy detector.

One problem with photoacoustic measurement is that the photoacoustic signal is proportional to the output of the incoming light. The output of the diode lasers, or quantum cascade lasers, normally used is insufficient for the sensitive measurement of some substances. In optical absorption spectroscopy, the approach of lengthening the light path is used to enhance sensitivity. So-called multipass detectors are used. In these detectors, the light is reflected multiple times through the measuring area. Mirrors that are correspondingly arranged are used for this purpose. After several reflections, the light beam is guided out of the measuring cell and directed towards a detector. To prevent interference in the measuring cell, the light beam is guided as a straight line folded together between the two windows from the inlet window to the exit window.

To increase the measuring sensitivity of photoacoustic reflectors, a multipass arrangement can also be chosen in which the excitation light is reflected multiple times across the measuring range. Approaches of this type are described in A. Miklos, J. Ng, P. Hess, A. H. Kung, "Application of a wavelength-amplitude double-modulation method in photoacoustic detection using a pulsed optical parametric oscillator," Journal de Physique IV, 125, 579-582, (2005), and A. Miklos, S-C. Pei and A. H. Kung, "Multipass acoustically open photoacoustic detector for trace gas measurements," Applied Optics 45, 2529-2534, (2006). One problem with such approaches is that the alignment of the multipass arrangement has to be relatively exact. Up to now, this has delayed the development of practical photoacoustic multipass detectors.

A photoacoustic measuring arrangement with an acoustic measuring cell is known from U.S. Pat. No. 3,938,365. Here, the excitation is generated by largely monochromatic radiation that causes pressure fluctuations which lead to standing waves in the measuring cell. The intensity of the excitation light is modulated thereby, with the modulation frequency corresponding to one of the natural acoustic oscillations. This document also discloses that longitudinal, radial and azimuthal modes can be excited in the cylindrical measuring cell.

SUMMARY OF THE INVENTION

The invention aims to develop a photoacoustic detector by which sensitive measurements can easily be made. Likewise, a corresponding measuring method is presented.

A photoacoustic multipass detector with a high level of measuring sensitivity can be provided in a simple manner with a device for photoacoustic detection having a cylindrical acoustic resonator. This resonator contains an arrangement for guiding the excitation light in such a manner that the sound wave excitable by the absorption of the excitation light is the second azimuthal resonance of the cylinder oscillation. To illustrate this, consider a cylinder in cross section. When, through suitable excitation expansions occur in opposing quarters of the circle that represents the cylinder cross section, whereas no expansion occurs in the quarters adjacent to the opposing quarters which also lie opposite each other, a corresponding sound wave is generated. Through the excitation, circle segments with a pressure elevated by the expansion are thus formed. The adjacent circle segments, which are larger, exhibit normal and not elevated pressure. A circulating sound wave can thus form in the cylinder from these differences in pressure. By selecting a suitable excitation frequency, i.e., the repetition frequency or modulation frequency of the light source, the second azimuthal resonance can be excited. This strongly amplifies the photoacoustic signal. The excitation light should be guided essentially perpendicular to the cylinder axis. This means that the excitation light can have a slight component motion parallel to the cylinder axis. An angle between the excitation light beam and the cylinder axis of 85° is therefore sufficient. Generally, the angle is nearly 90°. It should be noted that it is not ruled out that, with the excitation of the second azimuthal resonance of the cylinder oscillation, that other sound waves may be excited as well. It is essential to the invention to design the device such that primarily the second azimuthal resonance of the cylinder oscillation is excited, whereas other sound waves are only incidentally excited.

A suitable arrangement for guiding the excitation light is provided by four mirrors that are arranged in the cylinder. These mirrors are arranged in groups of respectively two mirrors disposed opposite one another such that the light is guided through the area of the central axis of the cylinder. The second azimuthal resonance of the cylinder oscillation can thereby be excited very effectively as a result.

The mirrors are preferably arranged such that the excitation light is guided by a first mirror to a second mirror lying opposite the first mirror. The second mirror is arranged such that the light passes from there to an adjacent third mirror. The light is then reflected by the third mirror to a fourth mirror lying opposite the third mirror. This fourth mirror is arranged next to the first mirror such that the light coming from the third mirror is reflected by the fourth mirror to the first mirror.

This allows an excitation to occur in the circle segments that lie between the mirrors. With this arrangement, no heating occurs in the remaining area of the cylinder, i.e., because light does not irradiate these areas.

To specifically excite the second azimuthal resonance of the cylinder oscillation, it is advantageous to arrange the mirrors such that the excitation light is guided from the first mirror to the second mirror and/or from the third mirror to the fourth mirror so as to intersect the central axis of the cylinder. This prevents areas of the cylinder from being heated and subsequently expanding where this is not desirable. This also prevents excitation in antiphase.

In order to excite the entire length of the cylinder, and not just one plane of the cylinder, it is advantageous for the excitation light to receive a component motion along the cylinder axis. To this end, it is possible, for example, to arrange the mirror along the entire relevant length of the cylinder. Thus, each of the mirrors can be of a corresponding length. If the exciting light beam is guided into the cylinder in such a manner that it has a component along the cylinder axis in the first reflection, this component will be retained in each reflection. The light therefore expands between the mirrors in the above-described manner and additionally travels along the cylinder axis. This ultimately causes the entire area of the cylinder to be irradiated. A larger area is therefore available in which the substances to be investigated can be located.

To suppress the background signal, acoustic quarter-wave filters can be arranged between the mirrors and the inner area of the acoustic cylindrical resonator. Despite the effective reflection on the mirrors, part of the light striking the mirrors is absorbed and not reflected. This absorption causes the surrounding area to be heated and hence produces an undesirable signal. To prevent sound waves with a frequency that corresponds to the frequency of the second azimuthal resonance of the cylinder oscillation from reaching the interior of the cylinder, and hence the sound pressure sensors, quarter-wave filters are arranged between the mirrors and the inner areas of the acoustic cylindrical resonator. These quarter-wave filters can have the form of small tubes open at both ends through which the light can pass unhindered. The length of the tubes corresponds to a quarter of the acoustic wavelength that the sound exhibits at a frequency corresponding to the second azimuthal resonance of the cylinder oscillation. These acoustic filters function to largely dampen the sound at this wavelength or frequency. For further information in this regard, one can refer to the relevant technical literature on acoustics.

The photoacoustic signal forming in the cylinder can be best detected when at least two sound pressure sensors are arranged such that when a second azimuthal resonance of the cylinder oscillation forms, one sound pressure sensor is located at the area of the maximum of the azimuthal cylinder oscillation and another sound pressure sensor is located at the area of the minimum of the azimuthal cylinder oscillation. The sound pressure sensors are normally close to the wall or are directly on the wall of the cylinder. With the measurement of the difference signal from the two sound pressure sensors, the sound signal can be doubled. Normally, microphones are used as the sound pressure sensors.

If plates with holes, functioning as quarter-wave filters, are used to close the top and/or bottom end of the cylindrical acoustic resonator, the gas to be investigated can flow in and out of the cylinder. At the same time, undesirable noise that could distort the measurement is prevented from entering the cylindrical acoustic resonator.

Alternatively, porous plates made, for example, of ceramic or sintered glass, can be attached to the first and/or second end of the cylindrical acoustic resonator. Such plates allow air to pass through and act in a sound-proofing manner.

If a cylinder with a diameter of approximately 60-80% of the diameter of the cylindrical acoustic resonator is connected to the first and/or second end of the cylindrical acoustic resonator, a sound propagation from the cylindrical acoustic resonator into the adjoining cylinder is prevented. With such an arrangement, the sound can be captured, as it were, within the resonator.

According to the invention, the arrangement lends itself to always use the same measure at both ends, i.e., to provide plates with holes at both ends, or porous plates at both ends. It is also possible, however, to use one measure at one end and a different measure at the other.

If the axis of the cylindrical acoustic resonator is at least partially vertical and a heater is provided, a thermally induced convection causes the gas, i.e., the gas to be investigated, to flow through the cylindrical acoustic resonator. In particular, it lends itself to place the heater in the top, and adjoining cylinder part. The heater is expediently located at the top and not at the bottom so that the gas to be examined is not heated before it is measured.

To protect the sound pressure sensor and the mirror from temperatures that may be too high, it is useful to employ cooling around the cylindrical acoustic resonator. This generally prevents the threshold temperature of the sound pressure sensors installed in the resonator wall from being exceeded. This enables the measurement to be carried out even in hot gas with reasonable expenditure in terms of cooling.

Another possibility is to install the microphones in the cooler area outside the resonator wall instead of in the hot side of the resonator wall facing the gas. In this case, the sound signal can be coupled to the sound pressure sensors by way of suitable acoustic quarter-wave resonators. Quarter-wave resonators are small tubes with a length corresponding to a quarter of the wavelength of the sound. In contrast to quarter-wave filters, which are open at both ends, one end of the quarter-wave resonator is closed. The sound pressure sensors are located at this closed end in this case.

The excitation light can be provided in a wavelength-modulated or intensity-modulated manner. A particularly high acoustic signal can be achieved by setting the frequency of the second azimuthal resonance as the modulation frequency.

A high photoacoustic signal can also be achieved by pulsed excitation light. The frequency of the second azimuthal resonance is preferably chosen as the pulse repetition frequency.

It is also possible to excite the second azimuthal resonance with individual pulses. With excitation by individual pulses, an oscillation automatically forms at the resonance frequency. The resonance is not amplified as is the case with excitation by a pulse repetition frequency corresponding to the resonance frequency. However, because the resonance frequency can be changed, for example, with the temperature of the photoacoustic cell, the pulse repetition frequency must be correspondingly adapted for resonant excitation. The associated expenditure is avoided by excitation using individual pulses.

Optical detectors, preferably two photodiodes, can be arranged in a manner which can detect excitation light scattered by particles. This is particularly useful when fine dust particles are to be investigated. Solid particles can be distinguished from absorbent gases by comparing the scattered light signal with the photoacoustic signal. In addition, the type of fine dust can be more precisely identified by measuring the scattered light. For example, the photoacoustic signal of strongly absorbent soot is higher compared to the scattered light signal of, e.g., lighter sand. Since the composition of fine dust is important with respect to the effects harmful to health, this additional information is advantageous.

The size distribution of particles, especially fine dust particles, can be determined by changing the pulse length and/or pulse repetition frequency.

The different thermal capacity of larger and smaller fine dust particles is thereby exploited. The larger a particle, the larger its mass and thermal capacity. Utilizing excitation with a light pulse—these are generally laser pulses—the particles are first heated by the absorption of light. Then, the particles release heat into the surrounding area. Heating the surrounding gas causes it to expand, which generates a pressure wave that is measurable as sound. Due to the cross section, and hence the larger absorption area, more light and hence more heat are absorbed in the larger particles. Since the effectively absorbent area increases approximately by the square of the diameter, but the thermal capacity that is proportional to the mass increases by the power of three of the diameter, a lower temperature increase occurs in larger particles. However as noted, overall more heat is stored in the larger particles. It takes longer for this heat to be released to the surrounding area than with smaller particles. The difference between the duration of the exciting pulse and the duration of the photoacoustic signal, at least the end of the photoacoustic signal, is therefore greater for larger particles than smaller particles. All of the particles are heated more by increasing the pulse duration. A size distribution can therefore be inferred by comparing several of photoacoustic signals at different light pulse lengths. This effect can be illustrated and determined by a calculation. In practice, however, it is always advantageous to calibrate the respective detector by measuring reference samples.

The size distribution of the fine dust particles can also be determined by changing the pulse repetition frequency. As mentioned, the particles are heated with each pulse and then release their heat into the surrounding area. The smaller particles cool down more than larger particles between the individual excitation pulses. Since only the respective change in temperature of the ambient air contributes to the photoacoustic signal, the photoacoustic signal is larger when the heat absorbed between individual excitation pulses is released into the surrounding area as completely as possible. If the pulse repetition frequency is increased, the larger particles cannot sufficiently release their heat into the ambient air between the individual excitation pulses, and thereby contribute less to the photoacoustic signal. Comparing the overall photoacoustic signal at larger and smaller pulse repetition frequencies can thus be used to infer the size distribution of the detected fine dust particles. This can also be illustrated by a calculation. To achieve precise measuring results, it is advantageous, however, to calibrate the detector with known samples.

The informative value of fine dust particle measurements can thus be increased relatively easily, since information on the size distribution of the particles is obtained in addition to information on their concentration. This is advantageous since the harmful effects of fine dust particles depend on their size. In addition, different particle sizes can also provide information on the source or the cause of the fine dust exposure.

The invention also provides for a photoacoustic detection device comprising a cylindrical acoustic resonator having an arrangement for guiding light essentially perpendicular to a cylinder axis in such a manner that a second azimuthal resonance of cylinder oscillation is excitable by absorption of the light.

The light may be one of excitation light and light that forms an X-shaped beam. The arrangement for guiding light may comprise mirrors that reflect the light. The mirrors may comprise two mirrors which reflect the light passing through the cylinder axis. The mirrors may further comprise two mirrors which reflect the light toward two other mirrors. The mirrors may comprise two mirrors which reflect the light toward two other mirrors. The mirrors may comprise one of four mirrors, two groups of two mirrors arranged opposite one another, a first mirror reflecting the light to a second mirror, the second mirror reflecting the light to a third mirror, the third mirror reflecting the light to a fourth mirror, whereby the light passes through the cylinder axis, and the fourth mirror reflecting the light to the first mirror, and four mirrors arranged to form two beams of the light which intersect the cylinder axis.

The mirrors may comprise a first mirror reflecting the light to a second mirror, the second mirror reflecting the light to an adjacent third mirror, the third mirror reflecting the light to a fourth mirror arranged adjacent the first mirror, and the fourth mirror reflecting the light to the first mirror. The mirrors may reflect the light along the cylinder axis.

The device may further comprise one of plural acoustic quarter-wave filters, an acoustic quarter-wave filter located between each mirror of arrangement for guiding light and an inner area of the acoustic cylindrical resonator, and four acoustic quarter-wave filters.

The device may further comprise one of plural devices for detecting a photoacoustic signal, at least two sound pressure sensors, one sound pressure sensor located in an area of maximum azimuthal cylinder oscillation and another sound pressure sensor located in the area of the minimum azimuthal cylinder oscillation, one sound pressure sensor located in a first area of the cylindrical acoustic resonator and another sound pressure sensor located in the second different area of the cylindrical acoustic resonator.

The device may further comprise one of a top end of the cylindrical acoustic resonator being closed with a plate having holes and serving as quarter-wave filter, a bottom end of the cylindrical acoustic resonator being closed with a plate having holes and serving as quarter-wave filter, and top and bottom ends of the cylindrical acoustic resonator each being closed with a plate having holes and serving as quarter-wave filter.

The device may further comprise one of a first end of the cylindrical acoustic resonator being acoustically sealed with a porous plate that allows air to pass through and act in a sound-proofing manner, a second end of the cylindrical acoustic resonator being acoustically sealed with a porous plate that allows air to pass through and act in a sound-proofing manner, and first and second ends of the cylindrical acoustic resonator each being acoustically sealed with a porous plate that allows air to pass through and act in a sound-proofing manner.

The device may further comprise one of a cylinder connected to a first end of the cylindrical acoustic resonator, the cylinder comprising a diameter of approximately 60% to 80% of a diameter of the cylindrical acoustic resonator, a cylinder connected to a second end of the cylindrical acoustic resonator, the cylinder comprising a diameter of approximately 60% to 80% of a diameter of the cylindrical acoustic resonator, and a cylinder connected to each of first and second ends of the cylindrical acoustic resonator, each cylinder comprising a diameter of approximately 60% to 80% of a diameter of the cylindrical acoustic resonator.

The cylinder axis of the cylindrical acoustic resonator may be at least partially vertical, and the device may further comprise a heater that is one of arranged to provide heating to the cylindrical acoustic resonator and arranged in a top adjoining a cylinder of the cylindrical acoustic resonator.

The device may further comprise one of a cooling device arranged to provide cooling to the cylindrical acoustic resonator, sound pressure sensors positioned such that a threshold temperature is not exceeded within a cooled wall, and plural acoustic quarter-wave resonators arranged to acoustically couple an inner area of the cylindrical acoustic resonator to sound pressure sensors located in a cooled area.

The light may be wavelength-modulated. The light may be intensity-modulated. A frequency of the second azimuthal resonance may be set as a modulation frequency. The light may comprise pulses.

The device may further comprising one of optical detectors, photodiodes, and devices arranged to detect the light scattered by particles located within the cylindrical acoustic resonator.

The device may further comprise one of the device is structured and arranged to determine a size distribution of particles in a gas, the device is structured and arranged to determine a size distribution of fine dust particles in a gas, and the device is structured and arranged to determine a size distribution of particles in a gas by changing at least one of a pulse length and a pulse repetition frequency.

The invention also provides for a method for photoacoustic detection using the device described above, wherein the method comprises guiding light into a cylindrical acoustic resonator in such a manner that a second azimuthal resonance of cylinder oscillation is excited as a sound wave.

The invention also provides for a method for photoacoustic detection, wherein the method comprises guiding light into a cylindrical acoustic resonator in such a manner that a second azimuthal resonance of cylinder oscillation is excited as a sound wave.

The invention also provides for a photoacoustic detection device comprising a cylindrical acoustic resonator comprising mirrors. The mirrors are structured and arranged to reflect light along a first path that intersects a cylinder axis of the cylindrical acoustic resonator and reflect light along a second path that intersects the cylinder axis of the cylindrical acoustic resonator

BRIEF DESCRIPTION OF THE DRAWINGS

The invention will be described below based on the attached figure wherein:

FIG. 3 schematically shows one porous end plate of the cylindrical detector allowing air to pass through;

FIG. 4 schematically shows another porous end plate of the cylindrical detector allowing air to pass through;

DETAILED DESCRIPTION OF THE INVENTION

Figure 1:
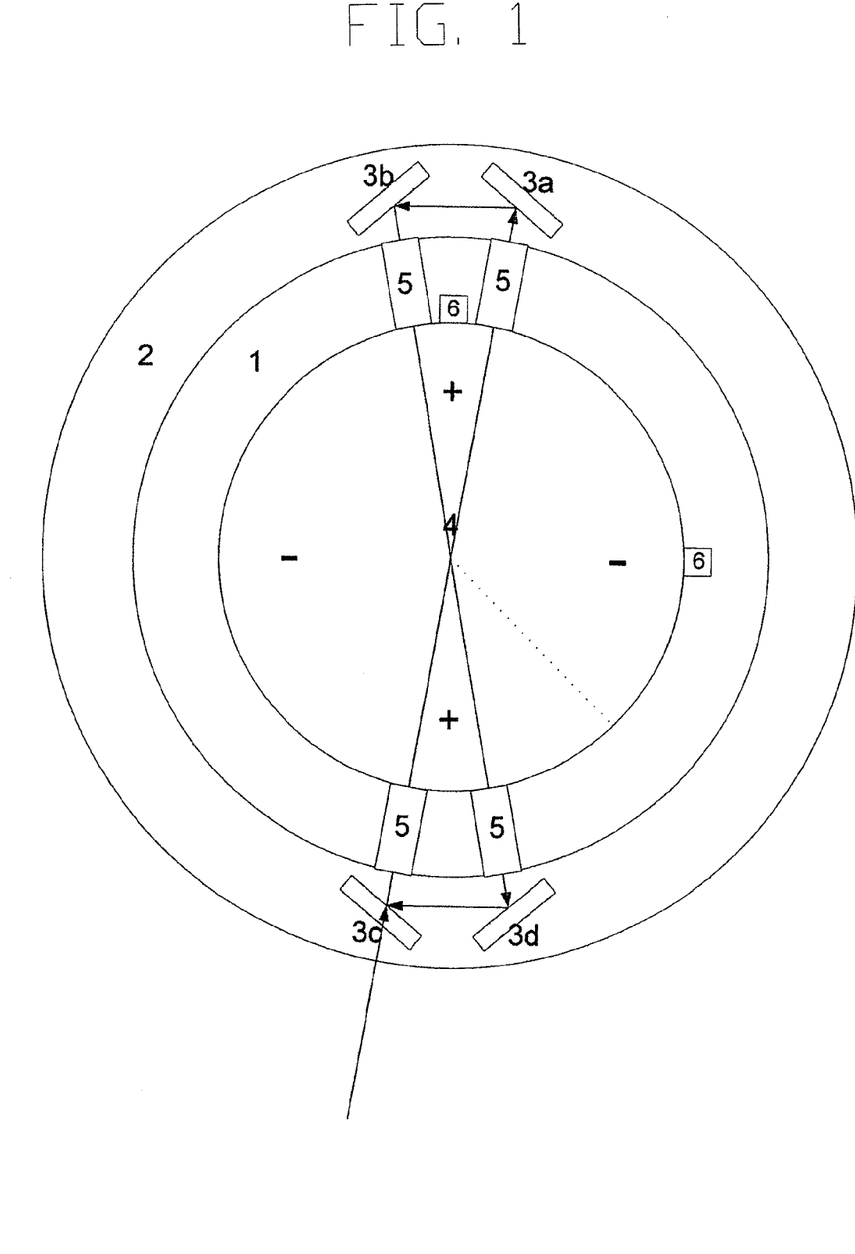
FIG. 1 shows a section view of a photoacoustic detector in accordance with the invention.

The invention is described in more detail below with reference to an exemplary embodiment without restricting the general application. FIG. 1 shows a section of a cylinder or cylinder ring 1 with the mirrors used in the photoacoustic detector. The cylinder 1 defines an interior space through light passes. Four mirrors 3a-3d are arranged to reflect light in the manner shown in the FIG. 1.

The mirrors 3a-3d are arranged in two groups of adjacent mirrors with one group including mirrors 3a and 3b and another group including mirrors 3c and 3d. The light enters next to the first mirror 3c and travels from there, intersecting the central axis of cylinder 1, to the opposite second mirror 3a. The light is then reflected from there to the adjacent third mirror 3b. The light is then reflected by mirror 3b, intersecting the central axis, back to the fourth mirror 3d and is then reflected from the minor 3d to the adjacent first mirror 3c. An X-shaped beam path 4 is thus formed by the mirrors 3a-3d. One can easily see that, as long as it contains at the beginning a component motion in the direction along the cylinder axis, the light will retain this component motion with each reflection off the mirrors 3a-3d. Accordingly, the light travels further in the cylinder along the cylinder axis. The X-shaped beam path 4 is likewise formed in each plane.

The device shown the drawings also utilizes quarter-wave filters 5 which can have the form of open tubes through which the light can pass unhindered. The length of the tubes corresponds to a quarter wavelength of the sound at the frequency of the second azimuthal resonance. These tubes efficiently dampen that wavelength or frequency of the sound. Although the mirrors 3a through 3d have a very good reflection—by virtue of the fact that these are gold-coated mirrors—a slight amount of absorption by the mirrors 3a to 3d is unavoidable. This absorption leads to heating and results in a sound wave that distorts the photoacoustic signal. The quarter-wave filters 5 ensure that the sound, at the frequency relevant to the photoacoustic signal, virtually does not reach the interior of the acoustic resonator. Two microphones 6 are shown in the figure. One of the microphones 6 is located between the mirrors 3b and 3a. This first microphone 6 is located at the beginning of the excitation of the sound wave, the area of highest sound pressure is located there. Another microphone 6 is located a quarter turn further on the wall of the cylinder 1. This is where the lowest sound pressure is found at the beginning of the excitation of a sound wave. The microphones 6, so positioned, can therefore measure a high difference signal. This difference signal is a gauge of the photoacoustic signal that is in the area irradiated by the light from the concentration of absorbent substances. Finally, as is apparent from the figure, the cylinder ring 1 is mounted on a base plate 2.

Figure 2:
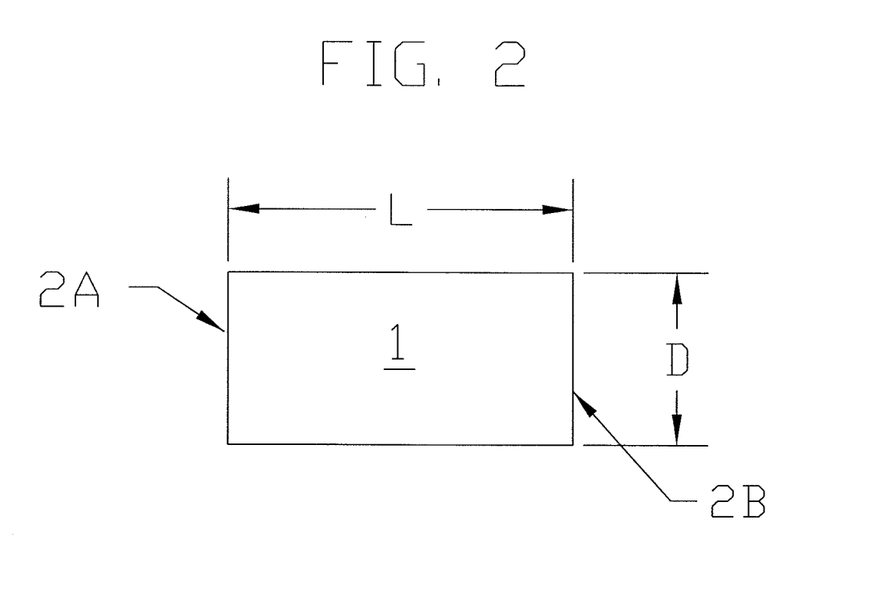
FIG. 2 schematically shows the cylindrical shape of the detector having a length and a diameter.
Figure 3:
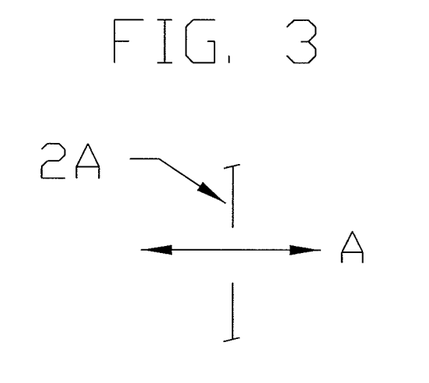
Figure 4:
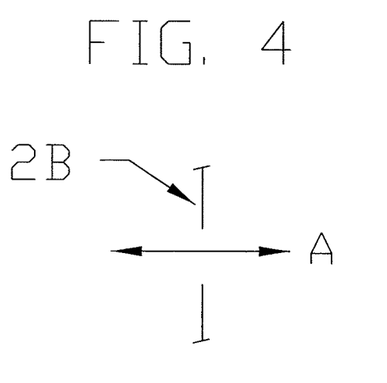

With reference to FIGS. 2-4, there is shown schematically the cylinder of the detector having a length L, a diameter D, and end plates 2A and 2B. FIGS. 3 and 4 show how each end plate 2A and 2B can be porous so as to allow air A to pass through.

Figure 5:
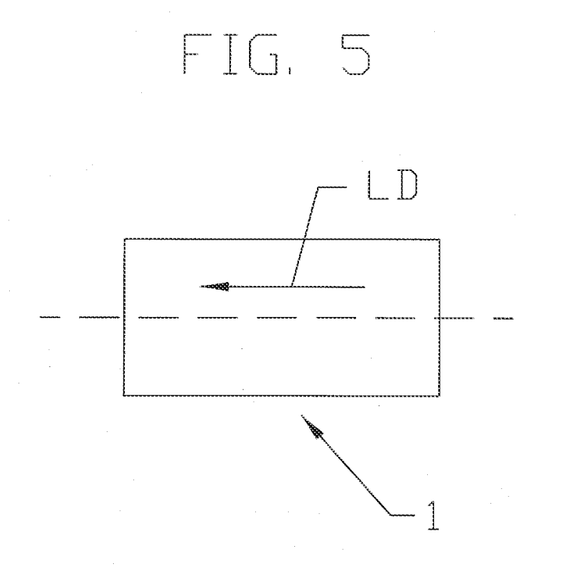
FIG. 5 schematically shows the cylindrical detector with light directed along an axis of the cylindrical detector.

With reference to FIG. 5, there is shown schematically the cylinder 1 of the detector having a center axis and showing a direction LD that light can be reflected along the cylinder axis.

Figure 6:
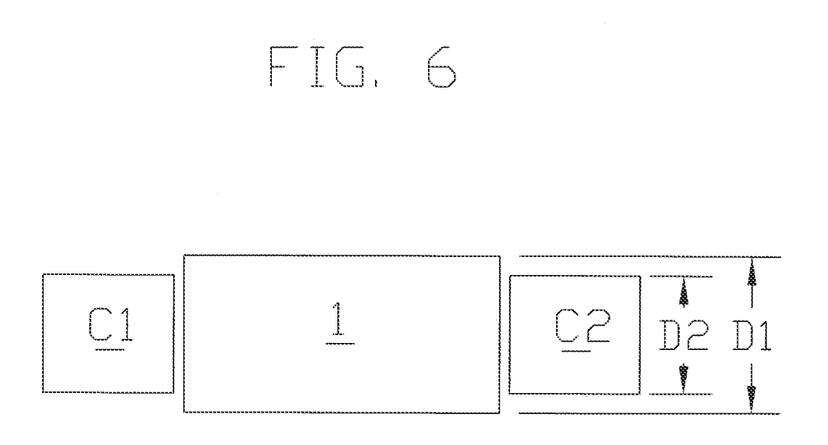
FIG. 6 schematically shows the cylindrical detector with smaller diameter cylinders arranged on first and second ends of the cylindrical detector.

With reference to FIG. 6, there is shown schematically the cylinder 1 of the detector having arranged on each of its first and second sized first and second cylinders C1 and C2 having a smaller diameter than that of the cylinder 1. In embodiments, diameter D2 of each of the first and second cylinders C1 and C2 is approximately 60% to 80% percent of the diameter D1.

Figure 7:
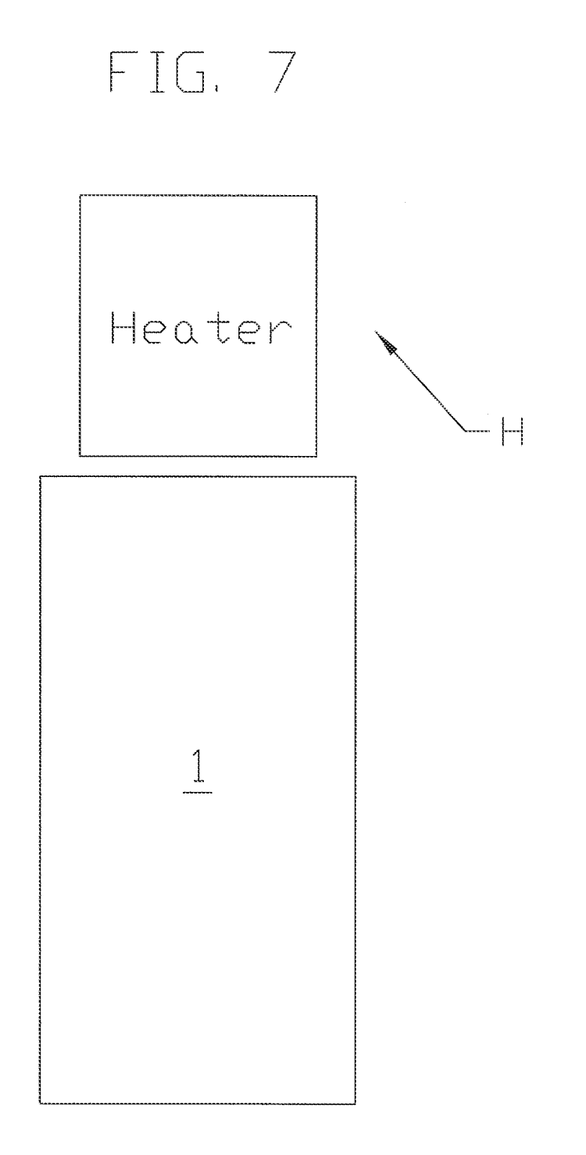
FIG. 7 schematically shows the cylindrical detector arranged vertically and with a heater arranged atop of the cylindrical detector.

With reference to FIG. 7, there is shown schematically the cylinder 1 of the detector arranged vertically and having arranged on a top end a heater H.

Figure 8:
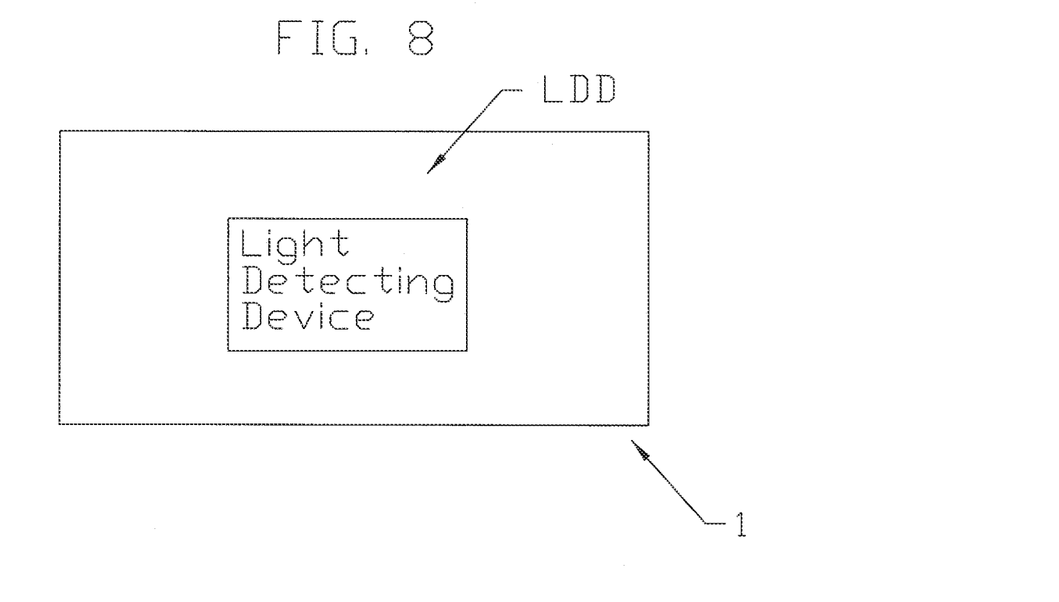
FIG. 8 schematically shows the cylindrical detector with a light detection device located within the cylindrical detector.

With reference to FIG. 8, there is shown schematically the cylinder 1 of the detector and having a light detecting device LDD arranged to detect light arranged within the cylinder 1. The device(s) LDD can be an optical detector(s) or photodiode(s).

Figure 9:
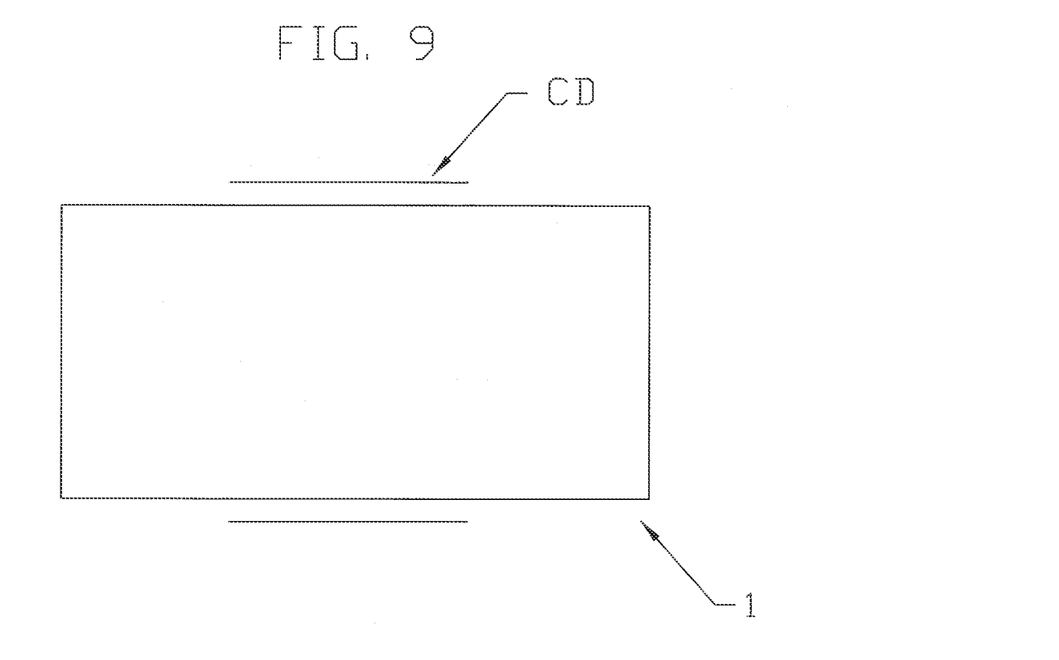
FIG. 9 schematically shows the cylindrical detector with a cooling device surrounding the cylindrical detector.

With reference to FIG. 9, there is schematically shown the cylindrical detector 1 with a cooling device CD surrounding the cylindrical detector 1.

LIST OF REFERENCE NUMBERS

1 Cylinder ring
2 Base plate
3a $2^{nd}$ mirror
3b $3^{rd}$ mirror
3c $1^{st}$ mirror
3d $4^{th}$ mirror
4 X-shaped beam path
5 Quarter-wave filter
6 Microphones
L Length
D Diameter
2A End plate
2B End plate
A Air
LD Light direction
C1 First cylinder
C2 Second cylinder
D1 Diameter of cylinder
D2 Diameter of smaller cylinder
H Heater
LDD Light detection device
CD Cooling device

The invention claimed is:
1. A photoacoustic detection device comprising:
a cylindrical acoustic resonator having an arrangement for guiding light essentially perpendicular to a longitudinal cylinder axis in such a manner that a second azimuthal resonance of cylinder oscillation is excitable by absorption of the light.
2. The device of claim 1, wherein the light is one of:
excitation light; or
light that fauns an X-shaped beam.
3. The device of claim 1, wherein the arrangement for guiding light comprises mirrors that reflect the light.
4. The device of claim 3, wherein the mirrors comprise two mirrors which reflect the light passing through the longitudinal cylinder axis.
5. The device of claim 4, wherein the mirrors further comprise two mirrors which reflect the light toward two other mirrors.
6. The device of claim 3, wherein the mirrors comprise two mirrors which reflect the light toward two other mirrors.
7. The device of claim 3, wherein the mirrors comprise one of:
four mirrors;
two groups of two mirrors arranged opposite one another;
a first mirror reflecting the light to a second mirror, the second mirror reflecting the light to a third mirror, the third mirror reflecting the light to a fourth mirror, whereby the light passes through the longitudinal cylinder axis, and the fourth mirror reflecting the light to the first minor; or
four mirrors arranged to form two beams of the light which intersect the longitudinal cylinder axis.
8. The device of claim 3, wherein the mirrors comprise:
a first mirror reflecting the light to a second mirror;
the second mirror reflecting the light to an adjacent third mirror;
the third mirror reflecting the light to a fourth mirror arranged adjacent the first mirror; and
the fourth mirror reflecting the light to the first mirror.
9. The device of claim 3, wherein a direction of the light has a component along a direction of the longitudinal cylinder axis.
10. The device of claim 1, further comprising one of:
plural acoustic quarter-wave filters arranged on the acoustic cylindrical resonator;
an acoustic quarter-wave filter located between each mirror of an arrangement for guiding light and an inner area of the acoustic cylindrical resonator; or
four acoustic quarter-wave filters arranged on the acoustic cylindrical resonator.
11. The device of claim 1, wherein the acoustic cylindrical resonator further includes therein or thereon one of:
plural devices for detecting a photoacoustic signal;
at least two sound pressure sensors;
one sound pressure sensor located in an area of maximum azimuthal cylinder oscillation and another sound pressure sensor located in the area of the minimum azimuthal cylinder oscillation;
one sound pressure sensor located in a first area of the cylindrical acoustic resonator and another sound pressure sensor located in the second different area of the cylindrical acoustic resonator.
12. The device of claim 1, further comprising one of:
a top end of the cylindrical acoustic resonator being closed with a plate having holes and serving as quarter-wave filter;
a bottom end of the cylindrical acoustic resonator being closed with a plate having holes and serving as quarter-wave filter; or
top and bottom ends of the cylindrical acoustic resonator each being closed with a plate having holes and serving as quarter-wave filter.
13. The device of claim 1, further comprising one of:
a first end of the cylindrical acoustic resonator being acoustically sealed with a porous plate that allows air to pass through and act in a sound-proofing manner;
a second end of the cylindrical acoustic resonator being acoustically sealed with a porous plate that allows air to pass through and act in a sound-proofing manner; or
first and second ends of the cylindrical acoustic resonator each being acoustically sealed with a porous plate that allows air to pass through and act in a sound-proofing manner.
14. The device of claim 1, further comprising one of:
a cylinder connected to a first end of the cylindrical acoustic resonator, the cylinder comprising a diameter of approximately 60% to 80% of a diameter of the cylindrical acoustic resonator;
a cylinder connected to a second end of the cylindrical acoustic resonator, the cylinder comprising a diameter of approximately 60% to 80% of a diameter of the cylindrical acoustic resonator; or
a cylinder connected to each of first and second ends of the cylindrical acoustic resonator, each cylinder comprising a diameter of approximately 60% to 80% of a diameter of the cylindrical acoustic resonator.

15. The device of claim 1, wherein the longitudinal cylinder axis of the cylindrical acoustic resonator is at least partially vertical, and further comprising a heater one of:
arranged to provide heating to the cylindrical acoustic resonator; or
arranged in a top adjoining a cylinder of the cylindrical acoustic resonator.

16. The device of claim 1, further comprising one of:
a cooling device arranged to provide cooling to the cylindrical acoustic resonator;
the cylindrical acoustic resonator is configured such that a threshold temperature is not exceeded within a cooled wall; or
an inner area of the cylindrical acoustic resonator being capable of acoustically coupling with plural acoustic quarter-wave resonators.

17. The device of claim 1, wherein one of:
the light is wavelength-modulated inside the cylindrical acoustic resonator;
the light is intensity-modulated inside the cylindrical acoustic resonator;
a frequency of the second azimuthal resonance is set as a modulation frequency inside the cylindrical acoustic resonator; or
the light comprises pulses inside the cylindrical acoustic resonator.

18. The device of claim 1, further comprising one of a following associated with the cylindrical acoustic resonator:
optical detectors;
photodiodes; or
devices arranged to detect the light scattered by particles located within the cylindrical acoustic resonator.

19. A method for photoacoustic detection using the device of claim 1, the method comprising:
guiding light into a cylindrical acoustic resonator in such a manner that a second azimuthal resonance of cylinder oscillation is excited as a sound wave.

20. The device of claim 1, wherein the light passes through at least one filter after passing through the central longitudinal cylinder axis, wherein the at least one filter dampens wavelength or frequency of sound.

21. A method for photoacoustic detection, the method comprising:
guiding light into a cylindrical acoustic resonator essentially perpendicular to a longitudinal cylinder axis of the cylindrical acoustic resonator in such a manner that a second azimuthal resonance of cylinder oscillation is excited as a sound wave.

22. The method of claim 21, passing the light through at least one filter after the light passes through the central longitudinal cylinder axis, wherein the at least one filter dampens wavelength or frequency of sound.

23. A photoacoustic detection device comprising:
a cylindrical acoustic resonator comprising mirrors;
the mirrors being structured and arranged to:
reflect light along a first path that intersects a central longitudinal cylinder axis of the cylindrical acoustic resonator; and
reflect light along a second path that intersects the central longitudinal cylinder axis of the cylindrical acoustic resonator.

24. The device of claim 23, wherein the light passes through at least one filter after passing through the central longitudinal cylinder axis, wherein the at least one filter dampens wavelength or frequency of sound.

* * * * *